United States Patent
Takizawa et al.

(10) Patent No.: US 9,198,557 B2
(45) Date of Patent: *Dec. 1, 2015

(54) ELECTRONIC ENDOSCOPIC APPARATUS

(75) Inventors: Kazuhiro Takizawa, Tokyo (JP); Motoo Azuma, Tokorozawa (JP); Hisashi Nishimura, Tokyo (JP); Kaoru Kotoda, Tokyo (JP); Satoshi Tanaka, Tokyo (JP); Takayuki Sato, Tokyo (JP); Naruyasu Kobayashi, Kawasaki (JP)

(73) Assignee: OLYMPUS CORPORATION, Tokyo (JP)

(*) Notice: Subject to any disclaimer, the term of this patent is extended or adjusted under 35 U.S.C. 154(b) by 420 days.

This patent is subject to a terminal disclaimer.

(21) Appl. No.: 13/527,113

(22) Filed: Jun. 19, 2012

(65) Prior Publication Data

US 2012/0320175 A1 Dec. 20, 2012

(30) Foreign Application Priority Data

Jun. 20, 2011 (JP) .................................. 2011-136407

(51) Int. Cl.
- H04N 5/06 (2006.01)
- A61B 1/00 (2006.01)
- A61B 1/04 (2006.01)

(52) U.S. Cl.
CPC .............. *A61B 1/00006* (2013.01); *A61B 1/04* (2013.01)

(58) Field of Classification Search
CPC ........................................................ A61B 1/04
USPC ........................................................... 348/65
See application file for complete search history.

(56) References Cited

U.S. PATENT DOCUMENTS

| 4,831,444 | A | * | 5/1989 | Kato | 348/518 |
| 5,255,092 | A | * | 10/1993 | Loonen | 348/718 |
| 5,585,840 | A | * | 12/1996 | Watanabe et al. | 348/65 |
| 7,248,281 | B2 | * | 7/2007 | Abe | 348/65 |
| 7,420,586 | B2 | | 9/2008 | Higuchi | |
| 7,485,091 | B2 | | 2/2009 | Abe | |
| 7,801,586 | B2 | | 9/2010 | Muratayev et al. | |
| 7,855,727 | B2 | * | 12/2010 | Adler et al. | 348/65 |
| 8,248,464 | B2 | * | 8/2012 | Takahashi | 348/65 |

(Continued)

FOREIGN PATENT DOCUMENTS

| JP | 2001-070241 A | 3/2001 |
| JP | 2001-275956 A | 10/2001 |

(Continued)

OTHER PUBLICATIONS

Office Action dated Feb. 3, 2015, issued in corresponding Japanese Application No. 2011-136407, with English Translation (4 pages).

(Continued)

*Primary Examiner* — William C Vaughn, Jr.
*Assistant Examiner* — Luis Perez Fuentes
(74) *Attorney, Agent, or Firm* — Westermann, Hattori, Daniels & Adrian, LLP

(57) ABSTRACT

A phase control unit compares a phase of a display synchronization signal with a phase of a clock signal generated from a clock signal generated by an imaging clock generating unit, and controls oscillation of the imaging clock generating unit based on a result of the comparison. A drive signal generating unit generates a drive signal that drives a CMOS sensor based on a multiplication clock signal synchronized to the clock signal.

6 Claims, 5 Drawing Sheets

(56) References Cited

U.S. PATENT DOCUMENTS

| | | | |
|---|---|---|---|
| 8,380,289 B2 | 2/2013 | Zellers et al. | |
| 8,558,880 B2 | 10/2013 | Nambakam et al. | |
| 8,970,686 B2 * | 3/2015 | Kobayashi et al. | 348/65 |
| 2006/0055793 A1 | 3/2006 | Adler et al. | |
| 2012/0320174 A1 * | 12/2012 | Sato et al. | 348/65 |
| 2012/0320175 A1 * | 12/2012 | Takizawa et al. | 348/65 |
| 2012/0320176 A1 * | 12/2012 | Tanaka et al. | 348/65 |
| 2012/0320177 A1 * | 12/2012 | Nishimura et al. | 348/65 |
| 2013/0016199 A1 * | 1/2013 | Kobayashi et al. | 348/65 |

FOREIGN PATENT DOCUMENTS

| | | |
|---|---|---|
| JP | 2004-049770 A | 2/2004 |
| JP | 2005-305124 A | 11/2005 |
| JP | 2006-288753 A | 10/2006 |
| JP | 2007-295096 A | 11/2007 |
| JP | 2009-061032 A | 3/2009 |

OTHER PUBLICATIONS

Non Final Office Action dated Sep. 11, 2014, issued in U.S. Appl. No. 13/527,098 (14 pages).

Office Action dated Feb. 3, 2015, issued in counterpart Japanese Patent Application No. 2011-136410, with English Translation (4 pages).

Notice of Allowance dated Mar. 30, 2015, issued in U.S. Appl. No. 13/527,098 (11 pages).

* cited by examiner

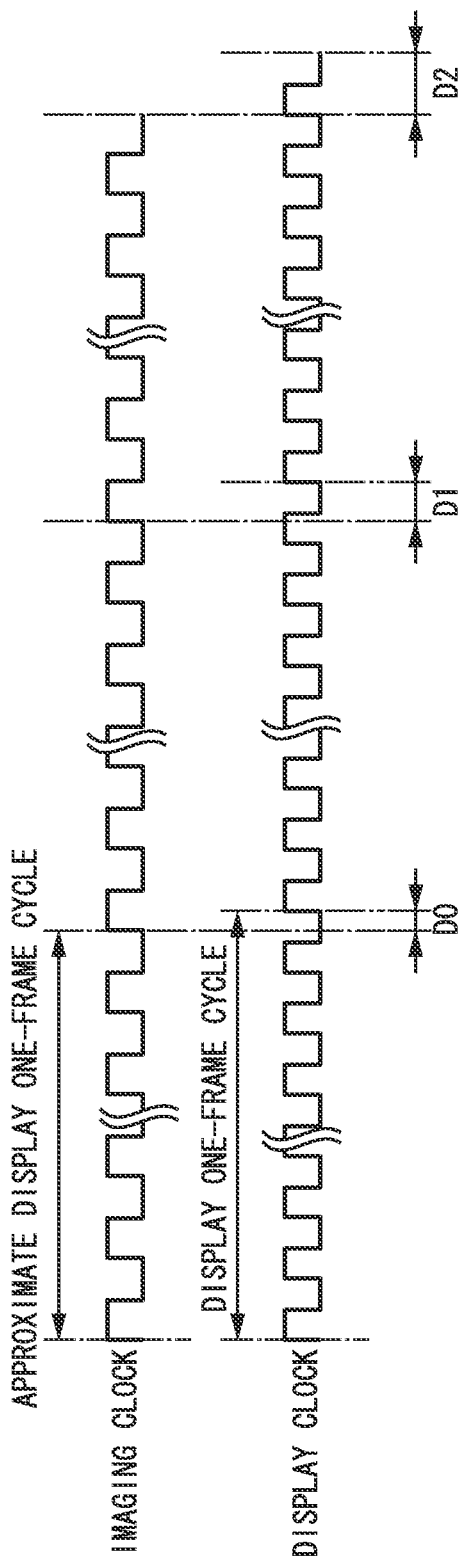

ELECTRONIC ENDOSCOPIC APPARATUS

BACKGROUND OF THE INVENTION

1. Field of the Invention

The present invention relates to an electronic endoscopic apparatus that includes an endoscopic scope on which a solid-state imaging device is mounted and an image processing processor performing predetermined image processing on an image signal from the endoscopic scope.

Priority is claimed on Japanese Patent Application No. 2011-136407 filed in Japan on Jun. 20, 2011, and the contents of which are incorporated herein by reference.

2. Description of Related Art

With the recent advancement of semiconductor technology, the number of pixels of a solid-state imaging device such as a Charge-Coupled Device (CCD) or Complementary Metal Oxide Semiconductor (CMOS) sensor is increasing.

Accordingly, electronic endoscopes, on which solid-state imaging devices are mounted and which have high definition, are increasing.

In an electronic endoscopic apparatus disclosed in Japanese Unexamined Patent Application Publication No. 2001-275956, a waveform smoothing circuit is inserted into an output portion of an electronic scope. Due to this waveform smoothing circuit, high-frequency noise released between the electronic scope and a processor device is inhibited.

FIG. 5 schematically shows a relationship between a one-frame cycle based on an imaging clock and a one-frame cycle based on a display clock.

SUMMARY OF INVENTION

According to a first aspect of the present invention, an electronic endoscopic apparatus includes an image processing processor and an endoscopic scope. Here, the image processing processor includes a display clock generating unit configured to generate a display clock, a display synchronization signal generating unit configured to generate a display synchronization signal based on the display clock, an imaging clock generating unit configured to generate a master imaging clock as a source that drives a solid-state imaging device, a multiplying/dividing unit configured to generate a first imaging clock by multiplying and/or dividing the master imaging clock and a second imaging clock by multiplying and/or dividing the master imaging clock, and a control unit configured to compare a phase of the display synchronization signal with a phase of the first imaging clock and control oscillation of the imaging clock generating unit based on a result of the comparison. Further, the endoscopic scope includes a solid-state imaging device configured to convert optical information into an electric signal and output the converted electric signal as an image signal, a multiplying unit configured to generate a multiplication imaging clock by multiplying the second imaging clock, and a drive signal generating unit configured to generate a signal that drives the solid-state imaging device based on the multiplication imaging clock.

According to a second aspect of the present invention, an electronic endoscopic apparatus includes an image processing processor and an endoscopic scope. Here, the image processing processor includes a display clock generating unit configured to generate a display clock, a display synchronization signal generating unit configured to generate a display synchronization signal based on the display clock, an imaging clock generating unit configured to generate a master imaging clock as a source that drives a solid-state imaging device, and a control unit configured to compare a phase of the display synchronization signal with a phase of the master imaging clock and control oscillation of the imaging clock generating unit based on a result of the comparison. Further, the endoscopic scope includes a solid-state imaging device configured to convert optical information into an electric signal and output the converted electric signal as an image signal, a multiplying unit configured to generate a multiplication imaging clock by multiplying the master imaging clock, and a drive signal generating unit configured to generate a signal that drives the solid-state imaging device based on the multiplication imaging clock.

According to a third aspect of the present invention, in the electronic endoscopic apparatus according to the first or second aspect of the present invention, the endoscopic scope may include an electro-optic converting unit configured to convert the image signal into an optical signal, and the image processing processor may include a photoelectric converting unit configured to convert the optical signal into the image signal.

Further, according to a fourth aspect of the present invention, in the electronic endoscopic apparatus according to the first or second aspect of the present invention, the endoscopic scope may include a converting unit configured to convert the image signal into a differential signal, and the image processing processor may include a demodulating unit configured to demodulate the differential signal into the image signal.

According to a fifth aspect of the present invention, in the electronic endoscopic apparatus according to the first or second aspect of the present invention, the endoscopic scope may include a wireless transmitting unit configured to wirelessly transmit the image signal, and the image processing processor may include a wireless receiving unit configured to receive the image signal that is wirelessly transmitted by the wireless transmitting unit.

According to a sixth aspect of the present invention, in the electronic endoscopic apparatus according to the first aspect of the present invention, the image processing processor may output the display synchronization signal to the endoscopic scope, and the drive signal generating unit may generate the drive signal based on the multiplication imaging clock and the display synchronization signal.

According to a seventh aspect of the present invention, in the electronic endoscopic apparatus according to the sixth aspect of the present invention, the display synchronization signal may be superimposed on the second imaging clock and be transmitted through a transmission line equal to that through which the second imaging clock is transmitted.

According to an eighth aspect of the present invention, in the electronic endoscopic apparatus according to the second aspect of the present invention, the image processing processor may output the display synchronization signal to the endoscopic scope, and the drive signal generating unit may generate the drive signal based on the multiplication imaging clock and the display synchronization signal.

According to a ninth aspect of the present invention, in the electronic endoscopic apparatus according to the eighth aspect of the present invention, the display synchronization signal may be superimposed on the master imaging clock and be transmitted through a transmission line equal to that through which the master imaging clock is transmitted.

According to a tenth aspect of the present invention, in the electronic endoscopic apparatus according to the first or second aspect of the present invention, the endoscopic scope may include a compressing unit configured to compress the image signal, and the image processing processor may include a decompressing unit configured to expand the image signal that is compressed by the compressing unit.

BRIEF DESCRIPTION OF THE DRAWINGS

FIG. 5 is a timing chart that explains a conventional electronic endoscopic apparatus.

DETAILED DESCRIPTION OF THE PREFERRED EMBODIMENTS

Hereinafter, embodiments of the present invention will be described with reference to the drawings.

First Embodiment

Figure 1:
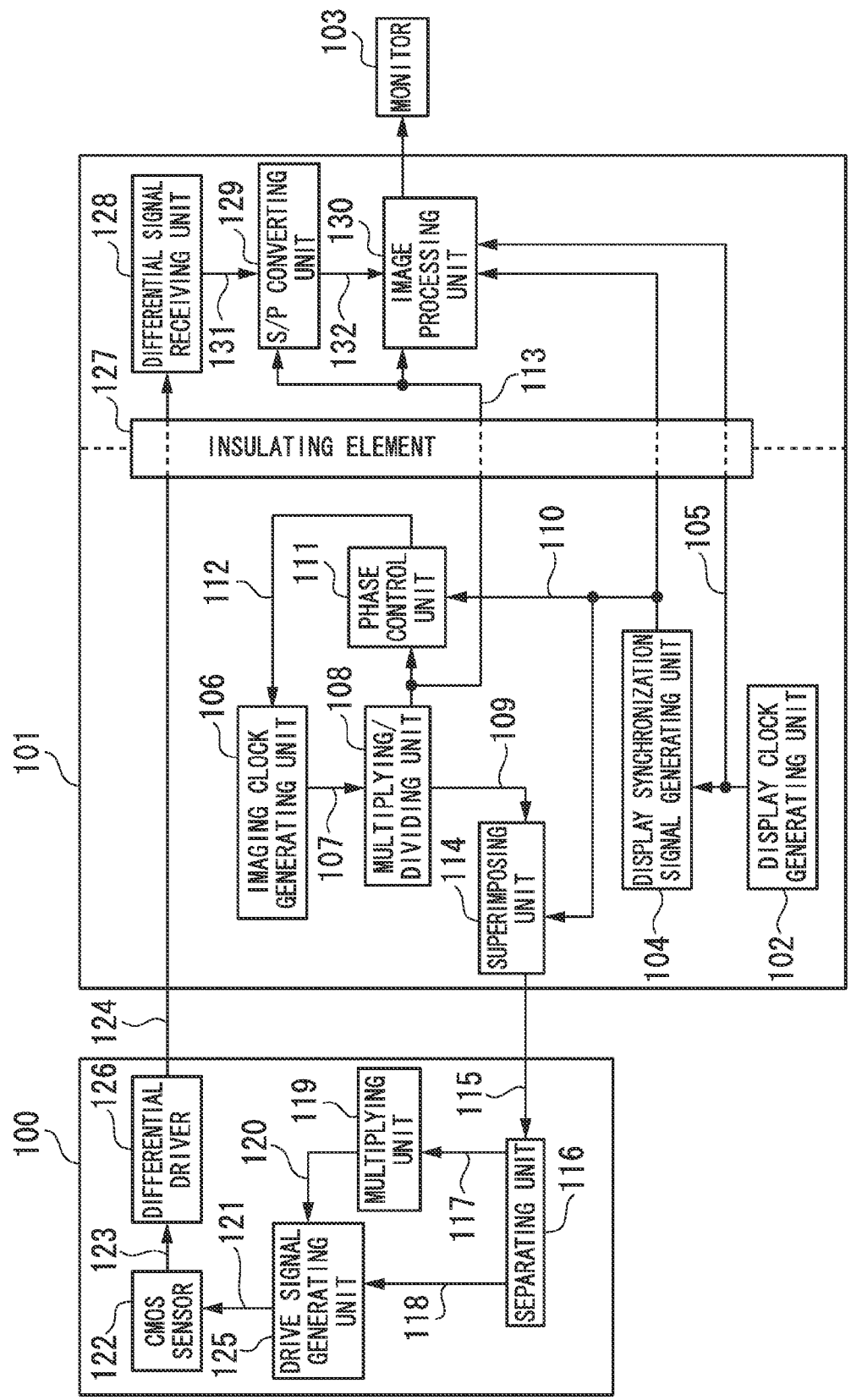
FIG. 1 is a block diagram showing a configuration of an electronic endoscopic apparatus according to a first embodiment of the present invention.

First, a first embodiment of the present invention will be described. FIG. 1 shows a configuration of an electronic endoscopic apparatus according to the present embodiment. The electronic endoscopic apparatus includes an endoscopic scope 100 and an image processing processor 101. The image processing processor 101 is connected to a monitor 103.

The endoscopic scope 100 includes a separating unit 116, a multiplying unit 119, a complementary metal oxide semiconductor (CMOS) sensor 122, a drive signal generating unit 125, and a differential driver 126. The image processing processor 101 includes a display clock generating unit 102, a display synchronization signal generating unit 104, an imaging clock generating unit 106, a multiplying/dividing unit 108, a phase control unit 111, a superimposing unit 114, a differential signal receiving unit 128, a serial-to-parallel (S/P) converting unit 129, and an image processing unit 130.

The display clock generating unit 102 of the image processing processor 101 generates a display clock signal 105. The display clock signal 105 is a display clock that drives each component pertaining to displaying. The display clock signal 105 is output to the display synchronization signal generating unit 104, and is simultaneously supplied to the image processing unit 130 through an insulating element 127 provided for safety of an examinee. The display synchronization signal generating unit 104 generates a display synchronization signal 110 on the basis of the display clock signal 105. The display synchronization signal 110 is a signal that complies with television standards to display an image on the monitor 103. To generate the display synchronization signal 110, the clock signal 105 generated by the display clock generating unit 102 is used. The display synchronization signal 110 is output to the phase control unit 111 and the superimposing unit 114, and is simultaneously supplied to the image processing unit 130 through the insulating element 127. The imaging clock generating unit 106 generates a clock signal 107. The clock signal 107 is a master clock as a source that drives the CMOS sensor 122.

The multiplying/dividing unit 108 appropriately performs only multiplication, only division, or a combination of the multiplication and the division on the clock signal 107 generated by the imaging clock generating unit 106, and generates a clock signal 109 and a clock signal 113. The clock signal 109 is a signal that is transmitted to the endoscopic scope 100. The clock signal 109 has a frequency lower than that of the clock signal 107 generated by the imaging clock generating unit 106. The clock signal 113 is output to the phase control unit 111, and is simultaneously supplied to the S/P converting unit 129 and the image processing unit 130 through the insulating element 127. The clock signal 113 has a frequency higher than that of the clock signal 107 generated by the imaging clock generating unit 106.

The phase control unit 111 compares a phase of the clock signal 113 with a phase of the display synchronization signal 110. On the basis of a result of the comparison, the phase control unit 111 outputs a control signal 112 to the imaging clock generating unit 106 to control an oscillation state of the clock signal 107 in the imaging clock generating unit 106. The imaging clock generating unit 106 controls the frequency of the clock signal 107 based on the control signal 112 such that the phase of the clock signal 113 is identical to the phase of the display synchronization signal 110. When the imaging clock generating unit 106 is mounted, an oscillator that can arbitrarily change a frequency using an external control signal may be used.

Figure 2:
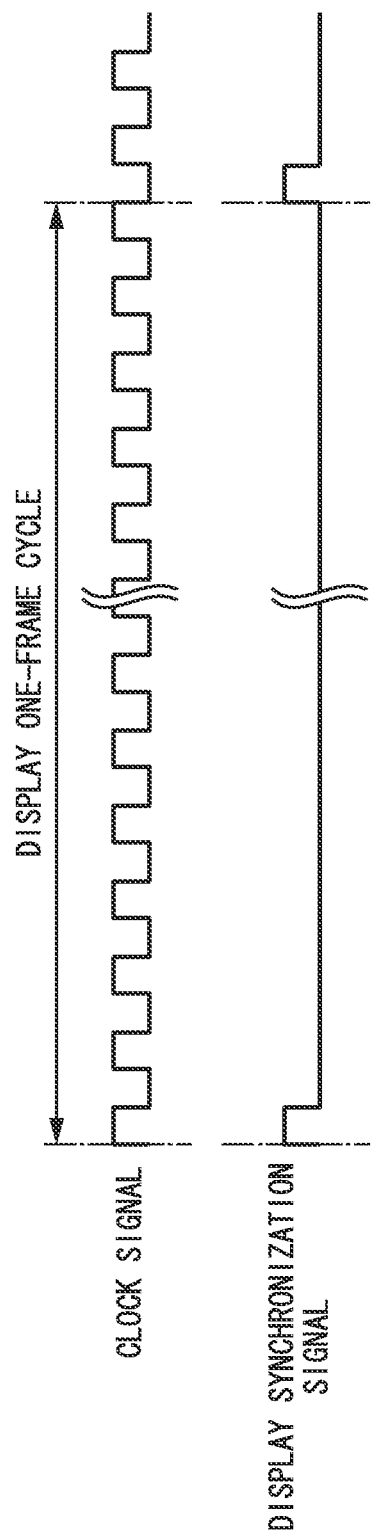
FIG. 2 is a timing chart that explains an operation of a phase control unit included in the electronic endoscopic apparatus according to the first embodiment of the present invention.

FIG. 2 shows operations of the phase control unit 111. The phase control unit 111 compares, for instance, an edge position of rising of the clock signal 113 with an edge position of rising edge of the display synchronization signal 110 (vertical synchronization signal in an example of FIG. 2). On the basis of a difference between the two edge positions, the phase control unit 111 outputs the control signal 112 to the imaging clock generating unit 106. On the basis of the control signal 112, the imaging clock generating unit 106 controls the oscillation state of the clock signal 107, that is, the frequency of the clock signal 107. Thereby, the edge position of rising of the clock signal 113 generated from the clock signal 107 is identical to the edge position of rising of the display synchronization signal 110. As a result, it is possible to secure the synchronization between the clock signal 107 and the display synchronization signal 110. In FIG. 2, the example in which the vertical synchronization signal is used when the phase thereof is compared with the phase of the clock signal 113 is shown. However, a horizontal synchronization signal may be used.

The superimposing unit 114 superimposes the display synchronization signal 110 on the clock signal 109 generated from the clock signal 107, and generates a clock signal 115. The clock signal 115 is output from the image processing processor 101, and is input to the separating unit 116 of a distal end of the endoscopic scope 100 through a transmission cable of the endoscopic scope 100. The separating unit 116 separates and outputs a clock signal 117 (corresponding to the lock signal 109) and a display synchronization signal 118 (corresponding to the display synchronization signal 110), both of which are included in the clock signal 115.

The multiplying unit 119 multiplies the clock signal 117 to thereby generate a multiplication clock signal 120. The drive signal generating unit 125 sets the multiplication clock signal 120 as an operation clock, and generates a drive signal 121 that drives the CMOS sensor 122. In this case, the display synchronization signal 118 is referred to as a signal that defines a start position of a frame. The CMOS sensor 122 converts optical information into an electric signal according to the drive signal 121, and outputs a serial type of image signal 123. The differential driver 126 converts the image signal 123 into a differential signal 124. The differential signal 124 output from the differential driver 126 is input to the image processing processor 101 through the transmission cable of the endoscopic scope 100.

In the image processing processor 101, the differential signal 124, which is input, is received through the insulating element 127 by the differential signal receiving unit 128. The differential signal receiving unit 128 demodulates the differential signal 124, which is received, to an image signal 131 of a serial type. The S/P converting unit 129 converts the image signal 131 of the serial type to an image signal 132 of a parallel type. The image signal 132 output from the S/P converting unit 129 is input to the image processing unit 130.

The image processing unit 130 performs switching of a clock signal for processing the image signal 132 from the clock signal 113 corresponding to an imaging clock to the display clock signal 105 using a buffer memory (so-called clock transfer). Furthermore, the image processing unit 130 performs a variety of image processing on the image signal 132 to display an image. In this case, the display synchronization signal 110 is referred to as a signal that defines a start position of a frame. The image signal processed by the image processing unit 130 is output to the monitor 103 and used when an image is displayed on the monitor 103.

In the present embodiment, the drive signal 121 that drives the CMOS sensor 122 is generated using the multiplication clock signal 120, the phase of which is identical to the phase of the display synchronization signal 118. As such, a phenomenon in which the imaging side and the displaying side have a difference in one-frame time does not occur. Further, when the imaging clock synchronized with the display clock is transmitted, the clock signal 109, a frequency of which is slower than an internal drive frequency (lower than an internal drive frequency), is generated and transmitted. As such, it is difficult for it to be affected by the signal degradation, and furthermore occurrence of electromagnetic noise can also be inhibited.

In the present embodiment, various modifications are possible. For example, the CMOS sensor is used as a solid-state imaging device in the present embodiment, but a charge-coupled device (CCD) may be used. Further, the CMOS sensor may mount a variety of processing circuits on the same chip. Accordingly, the drive signal generating unit 125 and the multiplying unit 119 of the present embodiment may be mounted on the same chip as the CMOS sensor.

As described above, according to the present embodiment, the phase control unit 111 controls the oscillation state of the clock signal 107 generated by the imaging clock generating unit 106 on the basis of the result of comparing the phase of the display synchronization signal 110 with the phase of the clock signal 113. As such, the display synchronization signal 110 and the clock signal 107 can be synchronized with each other. The drive signal 121 is generated from the multiplication clock signal 120 synchronized with the clock signal 107. Thereby, a one-frame cycle of the imaging and a one-frame cycle of the displaying are identical in length, and thus the synchronization between the imaging and the displaying can be secured.

Further, the clock signal 115, a frequency of which is lower than that of the clock signal 107, is transmitted from the image processing processor 101 to the endoscopic scope 100. As such, it is possible to reduce an influence caused by the speed-up of a signal such as the signal degradation and the occurrence of electromagnetic noise. Further, the differential signal is used to transmit the image signal, so that the resistance to disturbance noise can be increased.

Although the one-frame cycles at the imaging side and the displaying side are identical to each other as in the present embodiment, when the endoscopic scope and the image processing processor generate the synchronization signal and the drive signal at their own timings, frame start timings of the imaging side and the displaying side are not identical to each other. For this reason, there is a need to provide a buffer function to adjust the frame start timings. However, as in the present embodiment, when the drive signal generating unit 125 is instructed on the frame start of the imaging side by the display synchronization signal 118, the frame start timings of the imaging side and the displaying side can be identical to each other.

Further, when the display synchronization signal 110 is superimposed on the clock signal 109 and is transmitted to the endoscopic scope 100 using the same transmission line, the number of transmission lines can be reduced. As such, it is possible to reduce the diameter of the endoscopic scope 100.

Second Embodiment

Figure 3:
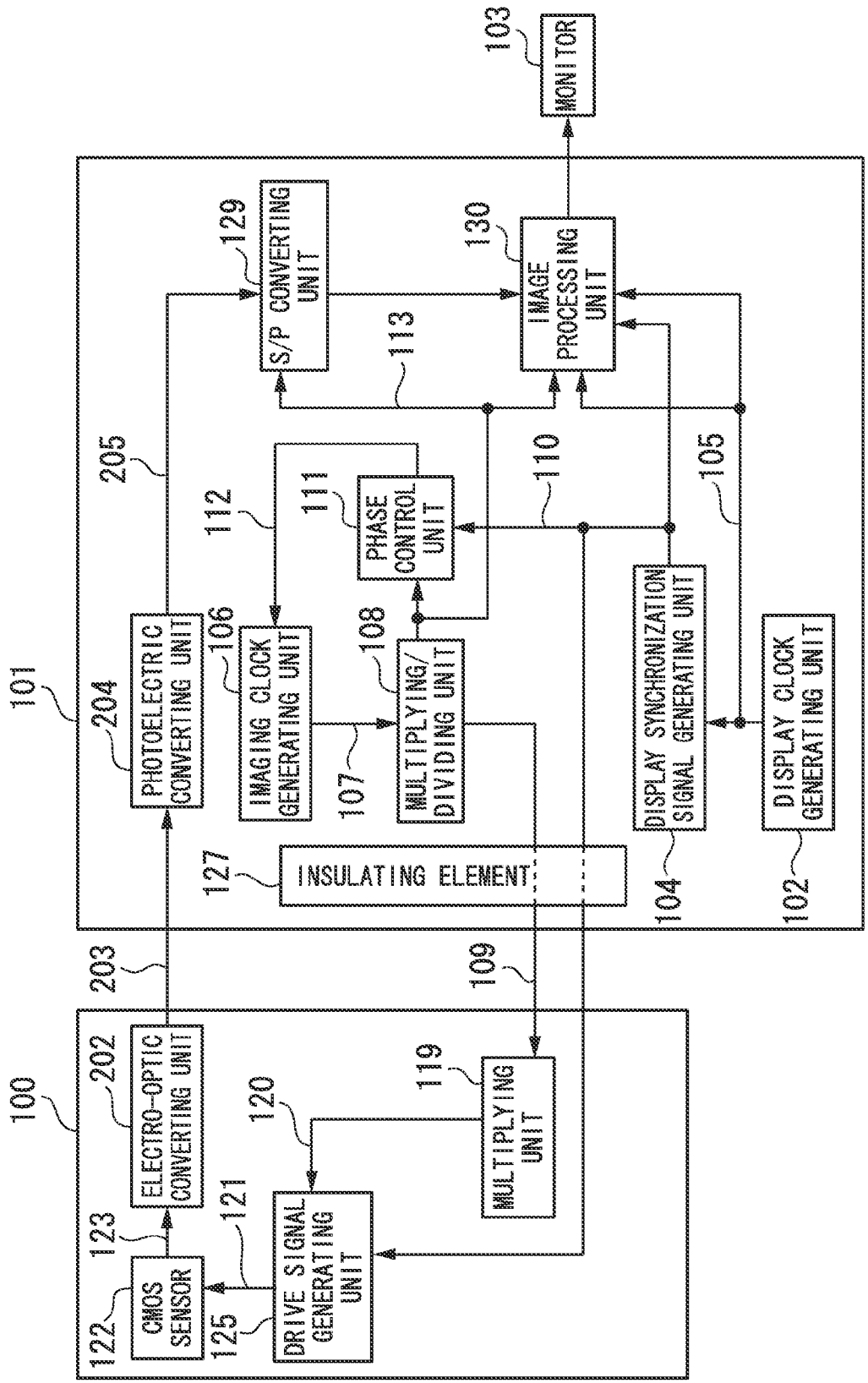
FIG. 3 is a block diagram showing a configuration of an electronic endoscopic apparatus according to a second embodiment of the present invention.

Next, a second embodiment of the present invention will be described. FIG. 3 shows a configuration of an electronic endoscopic apparatus according to the second embodiment. In FIG. 3, components having the same functions as those in the first embodiment are assigned the same symbols, and a description thereof will be omitted here.

In the present embodiment, similar to the first embodiment, an imaging clock generating unit 106 generates a clock signal 107 according to a control signal 112 generated by a phase control unit 111. Further, a multiplying/dividing unit 108 generates a clock signal 109 and a clock signal 113 from the clock signal 107. In the first embodiment, a display synchronization signal 110 is superimposed on the clock signal 109, and is output from an image processing processor 101. However, in the present embodiment, the display synchronization signal 110 is not superimposed on the clock signal 109, and the clock signal 109 is output from the image processing processor 101 through an insulating element 127, and is transmitted to an endoscopic scope 100. Similarly, the display synchronization signal 110 is also output from the image processing processor 101 through the insulating element 127 independently of the clock signal 109, and is transmitted to the endoscopic scope 100.

In the endoscopic scope 100, a multiplying unit 119 multiplies the clock signal 109 to generate a multiplication clock signal 120. The multiplication clock signal 120 is input to a drive signal generating unit 125. The drive signal generating unit 125 generates a drive signal 121 that drives a CMOS sensor 122 using the multiplication clock signal 120 and the display synchronization signal 110.

In the present embodiment, instead of the differential driver 126 and the differential signal receiving unit 128 that are used in the first embodiment, an electro-optic converting unit 202 and a photoelectric converting unit 204 are used. An image signal 123 output from the CMOS sensor 122 is converted into an optical signal 203 by the electro-optic converting unit 202, and is output to the image processing processor 101. In the image processing processor 101, the optical signal 203, which is input, is again converted into an image signal 205, which is an electric signal, by the photoelectric converting unit 204. Afterwards, similar to the first embodiment, image processing is performed by an image processing unit 130, and an image is displayed on a monitor 103.

In the present embodiment, improvement in resistance to disturbance noise caused by optical transmission and reduction in electromagnetic noise can be expected. Further, the clock signal and the display synchronization signal are transmitted by separate systems, and thus the signal lines required for transmission increase. However, a circuit inside the endoscopic scope 100 can be simplified.

In the present embodiment, various modifications are possible. For example, the clock signal 109 and the display synchronization signal 110, which are generated by the image processing processor 101, are transmitted to the endoscopic scope 100 through the insulating element 127. However, the insulating element 127 may be inserted into a position similar to that of the first embodiment. The optical transmission, however, can realize insulation in itself, and thus it is not necessary to newly insert an insulating element into a transmission line of image data. When a signal passes through the insulating element, it has no small effect on a quality of the signal. When the clock signal passes through the insulating element, there is a possibility of the degradation in the quality of the signal appearing as a jitter. A position where an oscillating function is provided may be determined in view of stable operation of a system.

Further, when the electro-optic converting unit 202 is inside the endoscopic scope 100, the electro-optic converting unit 202 may be mounted in any position. The electro-optic converting unit 202 may be mounted in any position selected from among a distal end of the endoscopic scope 100, a connection portion between the endoscopic scope 100 and the image processing processor 101, and an operating portion in which a user performs various operations. However, when the electro-optic converting unit 202 is disposed in any other position than the distal end, it is preferable to elaborate measures against a transmission line from the distal end to the electro-optic converting unit 202, for example, to transmit the image signal by means of the differential signal.

Further, in the present embodiment, the clock signal and the display synchronization signal are transmitted using separate signal lines. However, similar to the first embodiment, both signals may be superimposed and transmitted using one signal line.

As described above, according to the present embodiment, similar to the first embodiment, it is possible to secure synchronization between the imaging and the displaying. Further, the image signal is transmitted by means of the optical signal, so that the resistance to disturbance noise can be improved and electromagnetic noise can be reduced. Furthermore, an insulating process for securing the safety of a examinee can be easily performed.

Third Embodiment

Figure 4:
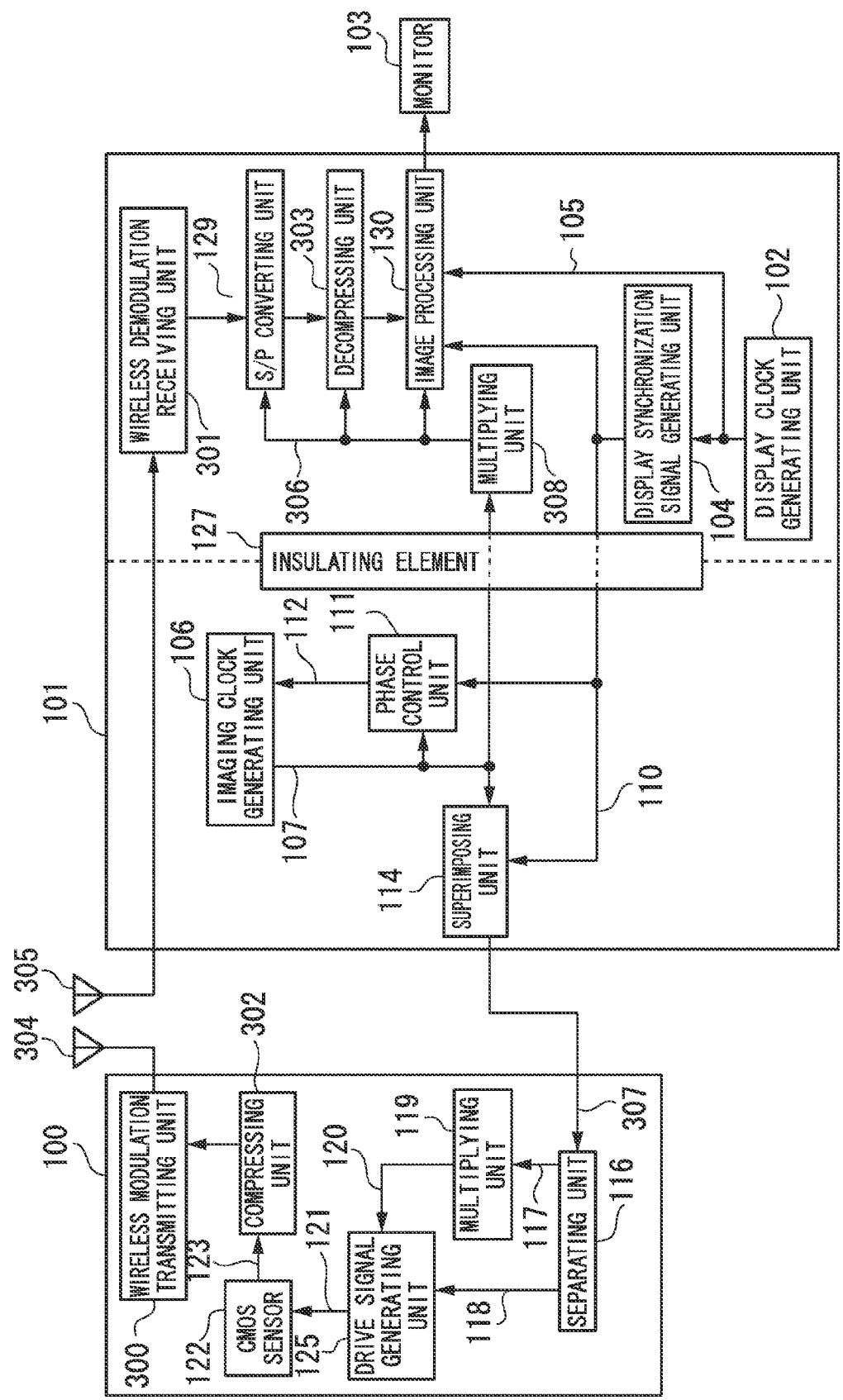
FIG. 4 is a block diagram showing a configuration of an electronic endoscopic apparatus according to a third embodiment of the present invention.

Next, a third embodiment of the present invention will be described. FIG. 4 shows a configuration of an electronic endoscopic apparatus according to the present embodiment. In FIG. 4, components having the same functions as those in the first or second embodiment are assigned the same symbols, and a description thereof will be omitted here.

In the present embodiment, similar to the first and second embodiments, an imaging clock generating unit 106 is controlled according to a control signal 112 generated by a phase control unit 111. However, in the present embodiment, a multiplying/dividing unit 108 is not provided, and a clock in which the phase control unit 111 uses for phase comparison with a display synchronization signal 110 is a clock signal 107 that is a master clock generated by the imaging clock generating unit 106. In comparison with the case of making a phase comparison with a clock having a higher frequency than the master clock as in the first and second embodiments, the phase of the clock signal is roughly adjusted in the present embodiment, but this adjustment suffices to prevent a phase shift between an imaging side and a displaying side.

Further, a superimposing unit 114 superimposes the display synchronization signal 110 on the clock signal 107, thereby generating a clock signal 307. The clock signal 307 is transmitted to an endoscopic scope 100. In the endoscopic scope 100, a clock signal 117 (corresponding to the clock signal 107) and a display synchronization signal 118 (corresponding to the display synchronization signal 110), which are included in the clock signal 307, are separated from each other by a separating unit 116.

Further, in the present embodiment, instead of the differential driver 126 and the differential signal receiving unit 128 used in the first embodiment, a wireless modulation transmitting unit 300, a wireless demodulation receiving unit 301, a compressing unit 302, a decompressing unit 303, an antenna 304, and an antenna 305 are used. The compressing unit 302 compresses an image signal 123 output from a CMOS sensor 122, thereby reducing an amount of data. The wireless modulation transmitting unit 300 transmits the compressed data as wireless data to an image processing processor 101 through the antenna 304.

In the image processing processor 101, the wireless demodulation receiving unit 301 receives the wireless data through the antenna 305. Then, an S/P converting unit 129 performs parallel conversion, and then the decompressing unit 303 expands the compressed data to restore original image data. For the parallel conversion by the S/P converting unit 129 and the expansion by the decompressing unit 303, a multiplication clock signal 306, into which a multiplying unit 308 multiplies the clock signal 107 generated by the imaging clock generating unit 106, is used. Afterwards, similar to the first embodiment, image processing is performed by an image processing unit 130, and an image is displayed on a monitor 103.

In the present embodiment, since a transmission line for transmitting the clock signal 307 is required, it is impossible to completely provide wireless connection between the endoscopic scope 100 and the image processing processor 101. However, by reducing signal lines required for data transmission, a diameter of the endoscopic scope 100 can be reduced. Further, similar to the second embodiment, since the wireless transmission can realize insulation in itself, the number of insulating elements can be reduced.

In the present embodiment, various modifications are possible. For example, in the present embodiment, the compressing and decompressing processes are applied to transmitting and receiving of the wireless data. However, when transfer capability of the wireless data is sufficiently high, the processes may not be applied. On the other hand, with respect to the first and second embodiments, the compressing and decompressing processes as in the present embodiment may be added. Similarly, in the present embodiment, the image processing processor 101 is not provided with the multiplying/dividing unit 108. However, similar to the present embodiment, the electronic endoscopic apparatus according to the first and second embodiments may not include the multiplying/dividing unit 108.

As described above, according to the present embodiment, similar to the first embodiment, it is possible to secure synchronization between the imaging and the displaying. Further, the image signal is transmitted by means of the wireless signal. Thereby, the number of signal lines required for the data transmission can be reduced, and the diameter of the endoscopic scope can be reduced. Further, an insulating process for securing the safety of a examinee can be easily performed. Further, the compressing and decompressing processes are applied. Thereby, the amount of data can be reduced, and particularly, a stable operation of wireless communication can be realized.

While the embodiments of the invention have been described in detail with reference to the drawings, specific configurations are not limited to these embodiments, and the present invention includes design modifications within a scope not departing from the gist of the present invention. The present invention is not limited by the descriptions above, but is limited only by the appended claims.

What is claimed is:

1. An electronic endoscopic apparatus comprising an image processing processor and an endoscopic scope,
    wherein the image processing processor comprises:
        a display clock generating unit configured to generate a display clock;
        a display synchronization signal generating unit configured to generate a display synchronization signal based on the display clock;
        an imaging clock generating unit configured to generate a master imaging clock as a source that drives a solid-state imaging device;
        multiplying-dividing unit configured to generate a first imaging clock by multiplying and/or dividing the master imaging clock and a second imaging clock by multiplying and/or dividing the master imaging clock; and
        a control unit configured to compare a phase of the display synchronization signal with a phase of the first imaging clock and control oscillation of the imaging clock generating unit based on a result of the comparison,
    wherein the image clock generating unit controls a frequency of the master imaging clock based on the result of the comparison such that the phase of the first imaging clock is identical to the phase of the display synchronization signal, and the endoscopic scope comprises:
        a solid-state imaging device configured to convert optical information into an electric signal and output the converted electric signal as an image signal;
        a multiplying unit configured to generate a multiplication imaging clock by multiplying the second imaging clock; and
        a drive signal generating unit configured to generate a signal that drives the solid-state imaging device based on the multiplication imaging clock,
    wherein the image processing processor outputs the display synchronization signal to the endoscopic scope, and
    the drive signal generating unit generates the drive signal based on the multiplication imaging clock and the display synchronization signal.

2. The electronic endoscopic apparatus according to claim 1, wherein the endoscopic scope comprises an electro-optic converting unit configured to convert the image signal into an optical signal, and
    the image processing processor comprises a photoelectric converting unit configured to convert the optical signal into the image signal.

3. The electronic endoscopic apparatus according to claim 1, wherein the endoscopic scope comprises a converting unit configured to convert the image signal into a differential signal, and
    the image processing processor comprises a demodulating unit configured to demodulate the differential signal into the image signal.

4. The electronic endoscopic apparatus according to claim 1, wherein the endoscopic scope comprises a wireless transmitting unit configured to wirelessly transmit the image signal, and
    the image processing processor comprises a wireless receiving unit configured to receive the image signal that is wirelessly transmitted by the wireless transmitting unit.

5. The electronic endoscopic apparatus according to claim 1, wherein the display synchronization signal is superimposed on the second imaging clock and is transmitted through a transmission line equal to that through which the second imaging clock is transmitted.

6. The electronic endoscopic apparatus according to claim 1, wherein the endoscopic scope comprises a compressing unit configured to compress the image signal, and the image processing processor comprises a decompressing unit configured to expand the image signal that is compressed by the compressing unit.

* * * * *